United States Patent [19]
Yamada et al.

[11] Patent Number: 5,867,807
[45] Date of Patent: Feb. 2, 1999

[54] METHOD AND APPARATUS FOR DETERMINATION OF OPTICAL PROPERTIES OF LIGHT SCATTERING MATERIAL

[75] Inventors: Yukio Yamada, Tsuchiura; Ryuichiro Araki, Sakado; Yutaka Yamashita, Hamamatsu, all of Japan

[73] Assignees: Agency of Industrial Science & Technology, Ministry of International Trade & Industry, Tokyo; Hamamatsu Photonics K.K., Hamamatsu, both of Japan

[21] Appl. No.: 738,110

[22] Filed: Oct. 25, 1996

[30] Foreign Application Priority Data

Oct. 26, 1995 [JP] Japan .................................. 7-300464

[51] Int. Cl.⁶ .................................................. G06F 19/00
[52] U.S. Cl. ............................................... 702/30; 702/22
[58] Field of Search ........................... 364/525; 600/310, 600/300; 356/442, 301, 433; 702/30, 22, 23; 250/306, 307, 341.1

[56] References Cited

U.S. PATENT DOCUMENTS

| | | | |
|---|---|---|---|
| 5,386,827 | 2/1995 | Chance et al. | 600/310 |
| 5,424,843 | 6/1995 | Tromberg et al. | 356/442 |
| 5,529,065 | 6/1996 | Tsuchiya | 600/310 |

*Primary Examiner*—James P. Trammell
*Assistant Examiner*—M. Kemper
*Attorney, Agent, or Firm*—Oblon, Spivak, McClelland, Maier & Neustadt, P.C.

[57] ABSTRACT

A method for determination of optical properties of light scattering material, includes calculating temporal changes in output light intensity with respect to a large number of combinations of reduced scattering coefficients $\mu s'$ and absorption coefficients $\mu a$ of a light-scattering material sample, storing the results, irradiating the sample with picosecond pulses of light and measuring temporal changes in the intensity of light coming out from the sample. When a measured temporal change in output light intensity is the same as or similar to a stored temporal change in intensity, the reduced scattering coefficient $\mu s'$ and absorption coefficient $\mu a$ of the stored temporal change in output light intensity are determined as the $\mu s'$ and $\mu a$ of the sample.

14 Claims, 8 Drawing Sheets

METHOD AND APPARATUS FOR DETERMINATION OF OPTICAL PROPERTIES OF LIGHT SCATTERING MATERIAL

BACKGROUND OF THE INVENTION

1. Field of the Invention

This invention relates to a method and apparatus for determining optical properties of light scattering material for use in various industries including materials, brewing, biomaterials, food, medicine and pharmaceuticals, and in the medical diagnostic field.

2. Description of the Prior Art

There are times when it is necessary to determine the optical properties of light scattering materials in order to establish the composition of slimes and fermentation suspensions in the brewing industry, of cosmetics, foodstuffs and non-transparent materials in the materials industry, and, in the pharmaceuticals and medical supplies industry, of non-transparent liquid products, creams and other semi-solid products as well as biological samples and solid products that can be sampled by crushing, cutting or slicing. A conventional way of determining the optical properties of a scattering body, when the target sample is large enough to be assumed to be an infinite medium or semi-infinite slab, with respect to light propagation, is to determine the equivalent scattering coefficient $\mu_s'$ and absorption coefficient $\mu_a$ of the sample by comparing the results of a time resolved determination and a theoretical analytical solution ("Determination of tissue optical parameters by time resolved analysis," Tsunazawa et al., 34th meeting of the Japan ME Society (1995)).

That method of determining optical properties is effective with respect to samples large enough to be assumed to be an infinite medium or semi-infinite slab or samples with a special geometrical shape such as a sphere or a cylinder. However, it cannot be used to quantify the optical properties of samples that are too small to apply an analytical solution to, such as samples that are too small to be assumed to be an infinite medium or semi-infinite slab and present many problems with respect to determining optical properties by the least squares method, and samples having an arbitrary shape. It also cannot be applied to samples having a distribution of optical properties.

In such cases optical properties can be determined by the Monte Carlo method, or finite-element method or other method of numerical analysis. However, the time required to perform the numerical calculations makes it difficult to implement the Monte Carlo or finite-element methods at the time of the analysis. One way of resolving this problem is to prepare a look-up table beforehand using a series of calculations based on the Monte Carlo method or numerical analyses, for a large number of conditions, and referring to this table during the analysis.

Thus, there has been a need for a way of readily determining optical properties of samples, even small or arbitrarily-shaped samples, or samples in which there is a distribution of optical properties.

An object of the present invention is to provide a method and apparatus for determining optical properties of light scattering material, even when a sample is too small to be assumed to be an infinite medium or semi-infinite slab with respect to light propagation, or is of an arbitrary shape, or has a distribution of optical properties.

SUMMARY OF THE INVENTION

To attain the above object, the present invention provides a method for determining optical properties of light scattering material, comprising:

a step of irradiating calculating and storing beforehand time response characteristics at a prescribed location on a scattering material sample in respect of numerous combinations of equivalent scattering coefficients and absorption coefficients;

a step of irradiating light pulses at the sample and measuring time response characteristics of output light at a prescribed point;

a step in which agreement or similarity between a measured time response characteristic and any stored time response characteristic is analyzed by comparing the characteristics; and a step in which an equivalent scattering coefficient and absorption coefficient of the sample are determined from an outcome of the analysis.

The calculations of the first step include calculations performed using the Monte Carlo method, finite-element method or other numerical analysis methods. The comparison analysis step includes calculating the log of the ratio of measured time response characteristics of output light to calculated time response characteristics for each time, and selecting a time response characteristic at which the calculation outcome is linear or can be regarded as linear relative to time.

The apparatus for determining optical properties of light scattering material according to the present invention comprises means for numerically calculating and storing beforehand time response characteristics at a prescribed location on a scattering material sample in respect of numerous combinations of equivalent scattering coefficients and absorption coefficients;

means of irradiating light pulses at the sample and measuring time response characteristics of output light at a prescribed point;

means of analyzing agreement or similarity between a measured time response characteristic and any stored time response characteristic by comparing the characteristics; and means of determining an equivalent scattering coefficient and absorption coefficient of the sample from an outcome of the analysis.

The analysis means includes means of calculating the log of the ratio of measured time response characteristics of output light to calculated time response characteristics for each time, and selecting a calculated time response characteristic at which the calculation outcome is linear or can be regarded as linear relative to time.

In accordance with the present invention the sample is irradiated with picosecond pulses of light and the light transmitted or reflected is measured using high-resolution time-resolved measurement. As such, even slight changes in the optical properties of a sample show up as changes in the results of time resolved measurements, allowing optical properties to be determined, even in the case of samples that are small, or have an arbitrary shape, or have a distribution of optical properties.

Further features of the invention, its nature and various advantages will be more apparent from the accompanying drawings and following detailed description of the invention.

BRIEF DESCRIPTION OF THE DRAWINGS

FIGS. 2 (a), 2 (b) and 2 (c) show an example of a look-up table for a sample in the apparatus of FIG. 1;

FIG. 4 (a) is a graph showing output intensity with respect to look-up table elements in FIG. 2 where $\mu a=0$ and $\mu s'=\mu s'_1$ plotted against temporal changes in the log of the ratio of the output light intensity of FIG. 3;

FIG. 4 (b) is a graph showing output intensity with respect to look-up table elements in FIG. 2 where $\mu a=0$ and $\mu s'=\mu s'_2$ plotted against temporal changes in the log of the ratio of the output light intensity of FIG. 3;

FIG. 4 (c) is a graph showing output intensity with respect to look-up table elements in FIG. 2 where $\mu a=0$ and $\mu s'=\mu s'_3$ plotted against temporal changes in the log of the ratio of the output light intensity of FIG. 3;

DESCRIPTION OF THE PREFERRED EMBODIMENT

Figure 1:
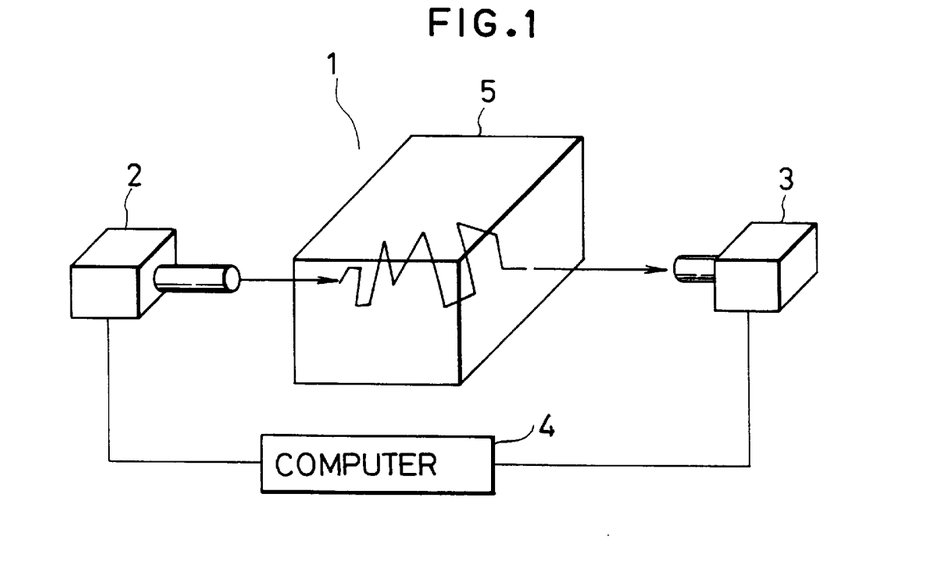
FIG. 1 shows the configuration of an embodiment of an apparatus for working the method of determining optical properties of light scattering material according to the present invention.

First, the apparatus used to implement the determination of optical properties of light scattering material according to the present invention will be described, with reference to the embodiment of the apparatus shown in FIG. 1. In FIG. 1, an apparatus 1 for determining optical properties includes a light source 2, a light detector 3 and a computer 4. A target sample 5 is placed between the light source 2 and the light detector 3.

Sample 5 may be a slime or fermentation suspension used in the brewing industry, a non-transparent material used in the materials industry, a non-transparent liquid product of the cosmetic, foodstuffs or pharmaceuticals and medical supplies industries, or a cream or other semi-solid product or solid product that can be sampled by crushing, cutting or slicing, a biological sample or any other material that has light-scattering properties, especially samples that are too small to be assumed to be an semi-infinite slab or infinite medium for light propagation, such as a sample with a diameter of 100 mm to 1 mm, or a sample having a distribution of optical properties.

The light source 2 can generate and irradiate the sample 5 with picosecond pulses of near-infrared light of a wavelength of 600 to 2000 nm. This wavelength region was selected because many substances in biological samples and in the food industry have an absorption spectrum in that range, such as hemoglobin, cyt. oxidase, protein, fat, and water and the like. A further reason is that non-invasive quantification of such substances can be considered to have a high industrial value. Pulses in the picosecond range are used because time resolved measurement of scattered light has to be done at a picosecond resolution. The light source 2 can be a pulsed diode laser for low output applications, or a titanium-sapphire laser for high output applications. Pulses of ultraviolet light or visible light may be used, depending on the sample.

The light detector 3 has to be an ultrahigh-speed detector with a time resolution in the picosecond range. A photomultiplier tube, ultrahigh-speed photodiode, optical oscilloscope and streak camera are examples of devices that can be used as the light detector 3.

Figure 2A:
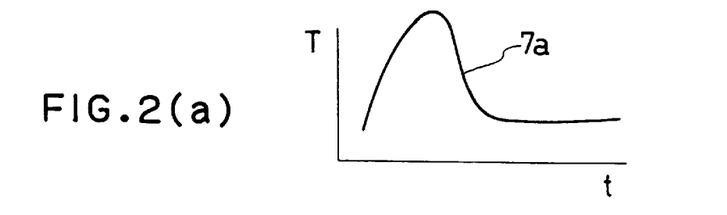
Figure 2B:
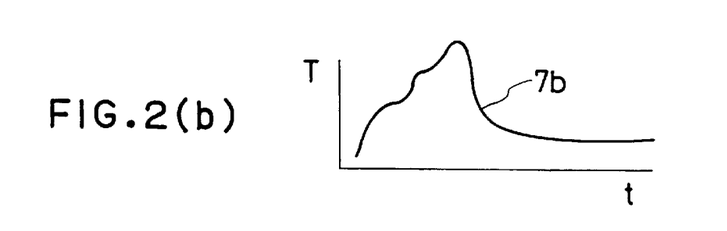
Figure 2C:
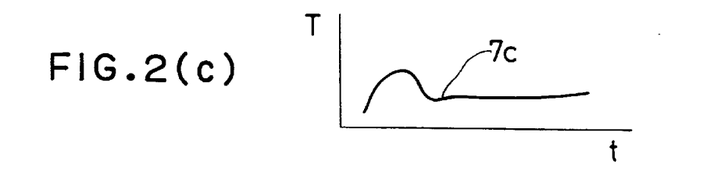

The method of the invention is worked as follows, using the apparatus 1. First, the computer 4 is used to calculate temporal changes in output light intensity by the Monte Carlo method, in respect of a large number of conditions and combinations of estimated reduced scattering coefficient $\mu s'$ and absorption coefficient $\mu a$ for a sample 5, such as, in the case of a tissue sample, $\mu s'=1.0$ mm$^{-1}$ and $\mu a=0.03$ mm$^{-1}$. A look-up table is formed of the temporal changes in output intensity for each $\mu s'$ and $\mu a$ combination i, i+1, i+2 ... and is stored in the computer 4. FIG. 2 shows an example of a look-up table, in which FIG. 2 (a) shows temporal change 7a in output light intensity at $\mu s'$ i, FIG. 2 (b) shows temporal change 7b in output intensity at $\mu s'$ i+1 and FIG. 2 (c) shows temporal change 7c in output intensity at $\mu s'$ i+2.

Figure 3:
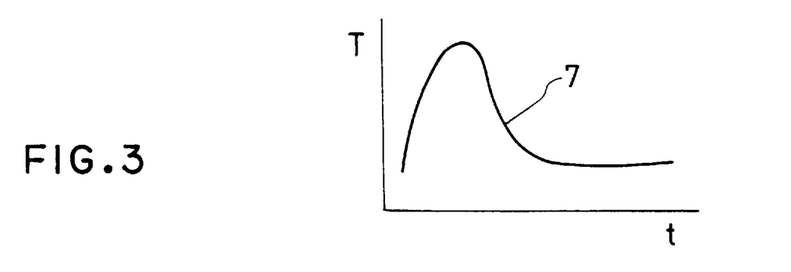
FIG. 3 shows an example of temporal changes in output light intensity.

Next, light pulses from the light source 2 are irradiated onto the sample 5 and temporal changes in the intensity of the light from the sample 5 are measured, using light detector 3. FIG. 3 shows an example of a temporal change 7 in the intensity of light from sample 5. Computer 4 is then used to compare the measured temporal change 7 with the temporal changes 7a, 7b and 7c stored in the computer 4. When there is agreement or similarity between temporal change 7 and any of temporal changes 7a, 7b and 7c, the reduced scattering coefficient $\mu s'$ and absorption coefficient $\mu a$ at the calculated temporal change (in this embodiment, temporal change in intensity 7a in FIG. 2 (a)) are determined as being the reduced scattering coefficient $\mu s'$ and absorption coefficient $\mu a$ of sample 5.

Figure 4A:
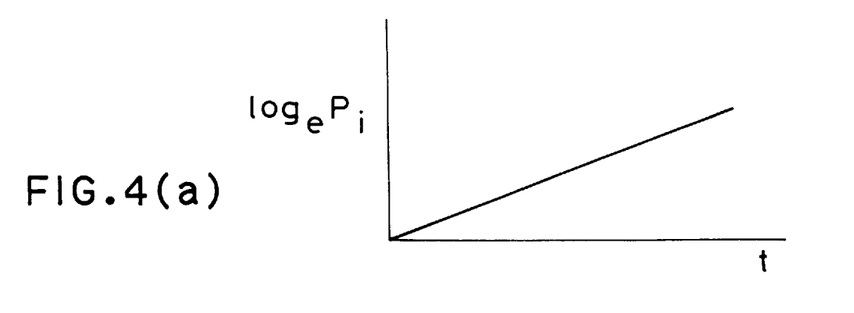
Figure 4B:
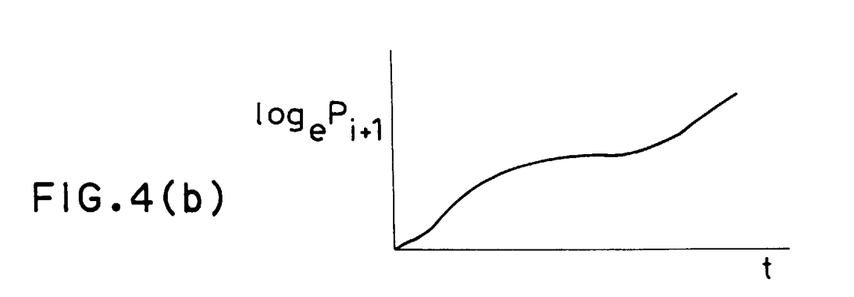
Figure 4C:
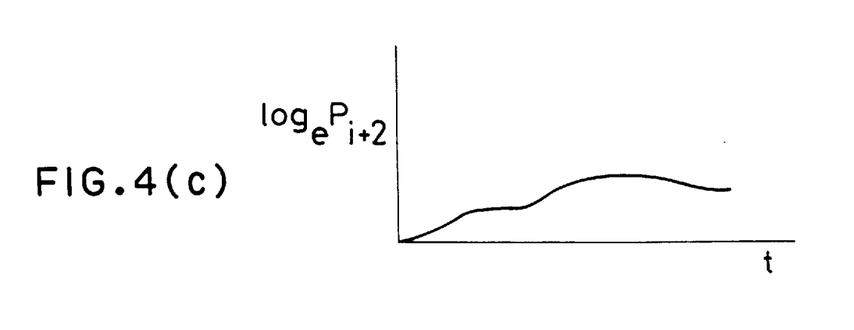

Also, the Monte Carlo method is used for calculations with regard to when there are many combinations of a reduced scattering coefficient $\mu s'$ with an absorption coefficient $\mu a$ of zero. The output light intensity at each time is calculated and stored in the computer 4, the sample 5 is subjected to pulsed light irradiation, output light intensity at each time is measured and the log is obtained of the ratio P of measured light intensity to stored light intensity. FIG. 4 (a) shows the log of the ratio of light intensity with respect to a FIG. 2 look-up table element $\mu a=0, \mu s'=\mu s'_1$ to the output light intensity 7 of FIG. 3; FIG. 4 (b) shows the log of the ratio of light intensity with respect to a FIG. 2 look-up table element $\mu a=0$, $\mu s'=\mu s'_2$ to the output light intensity 7 of FIG. 3; and FIG. 4 (c) shows the log of the ratio of light intensity with respect to a FIG. 2 look-up table element $\mu a=0$, $\mu s'=\mu s'_3$ to the output light intensity 7 of FIG. 3. When the temporal change of that log is a straight line, as in FIG. 4 (a), or almost straight, the scattering coefficient $\mu s'$ used to calculate the output light intensity is determined as being the scattering coefficient $\mu s'$ of the sample, and the sample's absorption coefficient $\mu a$ can also be determined from the slope m of the linear or almost linear temporal change of the log. That is, when a natural log, i.e. any of $\log_e(Pi)$, $\log_e(Pi+1)$, $\log_e(Pi+2)$ . . . of the ratio P of measured output light intensity to calculated output light intensity at each time is linear or almost linear relative to time, it is determined that the scattering coefficient $\mu s'$ used to calculate the output light intensity is the scattering coefficient $\mu s'$ of sample 5. Also, if m is the slope of the line, then the absorption coefficient $\mu a$ of the sample is determined as $\mu a=m/c$ (where c is the velocity of light in the medium; in tissue, for example, c=0.23 mm/ps). This method can reduce the amount of time-consuming calculations required to apply the Monte Carlo method to the large number of combinations of scattering and absorption coefficients $\mu s'$ and $\mu a$.

Figure 5:
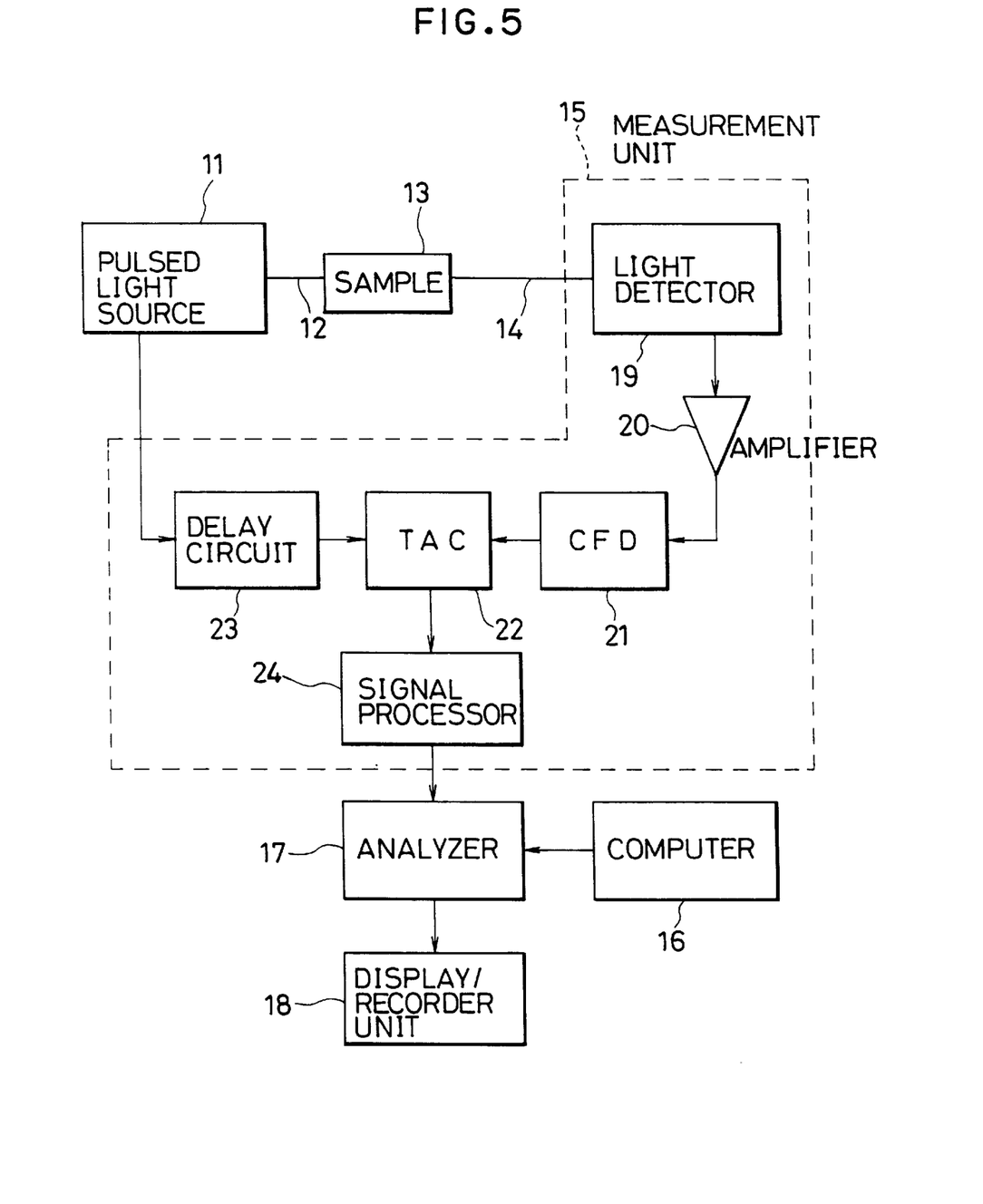
FIG. 5 shows the configuration of another embodiment of an apparatus for working the method of determining optical properties of light scattering material according to the present invention.

FIG. 5 shows the configuration of another embodiment of the apparatus of the present invention. The apparatus comprises a pulsed light source 11 for irradiating a target sample 13 with light pulses of a prescribed wavelength, a measurement unit 15 that detects light reflected or transmitted by the sample 13, a computer 16 for prior calculation and storage of time response characteristics for various optical parameters, an analyzer 17 that compares the time response characteristics of light reflected or transmitted by the sample 13 with the time response characteristics of the optical parameters calculated by the computer 16, and a display/recorder unit 18 for displaying and recording the output of the analyzer 17.

The light source 11 emits light in pulses having a width that is sufficiently shorter than the light expected to be transmitted or reflected by the sample 13. For this, the light source 11 may be a solid laser such as a titanium-sapphire laser or glass laser, a liquid laser such as a dye laser, or a gas laser such as a $N_2$ laser, or a semiconductor laser may be used. An optical fiber 12 guides the light from the light source 11 to the sample 13. Scattered light from the sample is guided by an optical fiber 14 to a light detector 19. The optical fiber 14 is positioned at a prescribed distance from the sample. The light detector 19, which is able to detect single photons, may be a photodiode, an avalanche diode, a phototube or a photomultiplier. For high-precision measurement of light from the sample 13, the frequency response of the light detector 19 should be as high as possible. Since the intensity of the light source 11 has been adjusted so that the light falls on the light detector 19 in a single photon event, it is possible to utilize the time correlated single photon counting method of measurement. Output signals by the light detector 19 are amplified to a prescribed strength of voltage by a signal amplifier 20 and input to a Constant Fraction Discriminator (CFD) 21. When the signal has reached a specific level, after the lapse of a prescribed time the CFD 21 outputs a start signal to a Time to Amplitude Converter (TAC) 22. The TAC 22 outputs a time correlated signal with an amplitude that is proportional to the time differential between the start signal from the CFD 21 and a light source 11 stop signal with a suitable delay applied by a delay circuit 23. A signal processor 24 sorts the time correlated signals from the TAC 22 for each time period (I/n), analyzing the pulse height while storing the signals in n memory locations. This enables the pulse height frequency distribution of the time correlated signals to be output to the analyzer 17 as a time spectrum. (I is the TAC maximum conversion time.)

The computer 16 uses the Monte Carlo method or other such method to calculate the output light characteristics of the sample 13 for various combinations of the reduced scattering and absorption coefficients, based on the shape of the sample 13 and the installation conditions of optical fibers 12 and 14 relative to sample 13. The results of these calculations are stored in the form of the table of FIG. 6. The analyzer 17 compares the output of the signal processor 24 to the calculated results in the FIG. 6 table stored in the computer 16 to establish whether any time response characteristics are the same or similar. Based on the outcome of this analysis, the analyzer 17 determines the reduced scattering coefficient and absorption coefficient for the sample 13, and outputs the coefficients to the display/recorder unit 18.

Figure 6:
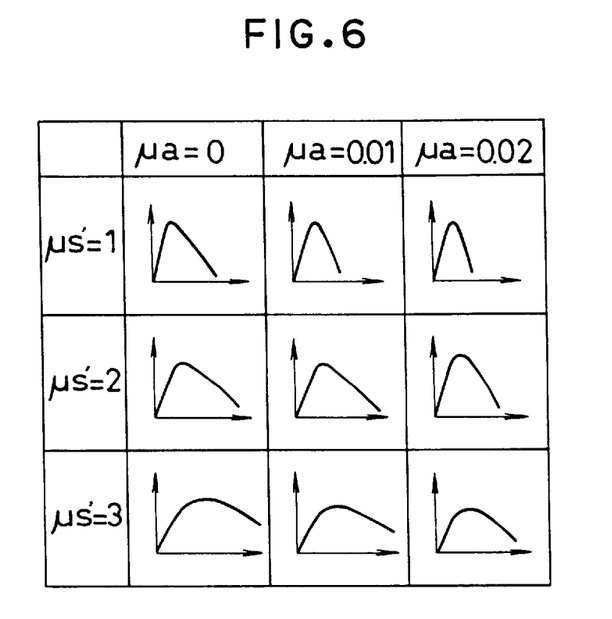
FIG. 6 shows an example of a look-up table for a sample, stored beforehand in the calculation section of the apparatus of FIG. 5.

Another identification method comprises calculating the log of the ratio of the output of the signal processor 24 to the $\mu a=0$ entry of the table in the computer 16 (in FIG. 6, the elements in the $\mu a=0$ column), and when the result is a straight line or can be regarded as a straight line, taking the reduced scattering coefficient used to calculate the elements at that time as the reduced scattering coefficient of sample 13. Also, if the straight line f(t) at that time is $$f(t) = at + b \qquad (1)$$

then $$\frac{df(t)}{(dt)} = a = \mu a C \qquad (2)$$

and absorption coefficient $\mu a$ can be calculated by $$\mu a = \frac{1}{C} \cdot \frac{df(t)}{dt} \qquad (3)$$

and is output to the display/recorder unit 18 as the absorption coefficient of sample 13. In the above equations (1) to (3), t is time and C is the velocity of light in the sample 13.

The method of using numerical analysis to calculate a sample's reduced scattering coefficient $\mu s'$ and absorption coefficient $\mu a$ will now be described. As with the Monte Carlo method, a look-up table is prepared containing temporal changes in output light intensity for various combinations of reduced scattering coefficient $\mu s'$ and absorption coefficient $\mu a$ estimated with respect to a sample of a certain shape. The following explanation relates to the use of the finite-element method of analysis to obtain temporal changes in output light intensity.

The behavior of light in a scattering material is expressed by the following photon diffusion equation.

$$\frac{1}{C} \frac{\partial \phi}{\partial t} = D\nabla^2 \phi - \mu a \phi + q \qquad (4)$$

Figure 7:
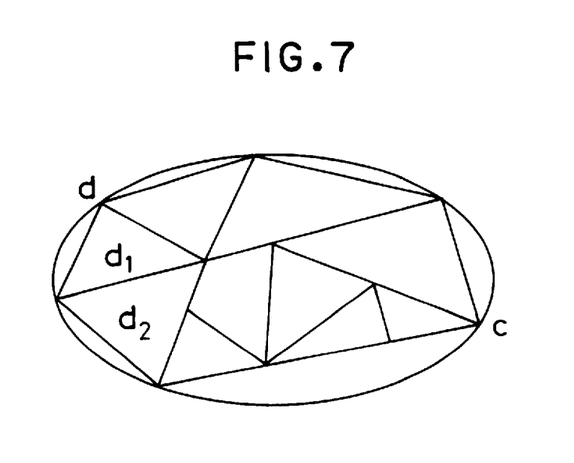
FIG. 7 is a diagram illustrating the finite-element method.

Here, C is the velocity of light in the scattering material, $\phi$ is the fluence rate, D is the diffusion coefficient, which is ⅓ $\mu s'$, and q is the light source. To solve this partial differential equation for a given boundary condition, there is the widely-known finite-element method, a method of obtaining an approximate solution within a region d enclosed by boundary c, as shown in FIG. 7, by dividing region d into a number of small, discrete regions $d_1$, $d_2$, that is, into elements of a finite size.

The photon density distribution P in these elements is shown by equation (5).

$$P(x, y, z, t) = [N(x, y, z)]\{\phi(t)\} \quad (5)$$

Here, [N(x, y, z)] is an interpolation function matrix linking element photon densities with nodal photon densities in a set of three-dimensional rectangular coordinates. $\{\phi(t)\}$ is nodal photon density vector at time t. With matrix [N] as a weighting function, the photon density $\phi$ at a desired point can be found by applying Galerkin's method. Also, based on Fick's law, flux vector J for photon density will be as shown in equation (6).

$$J = -D \cdot \text{grad}\{\phi\} \quad (6)$$

A look-up table of temporal changes in output light intensity for the reduced scattering coefficients $\mu s'$ and absorption coefficients $\mu a$ of various samples can be prepared by applying the method of this invention.

Figure 8:
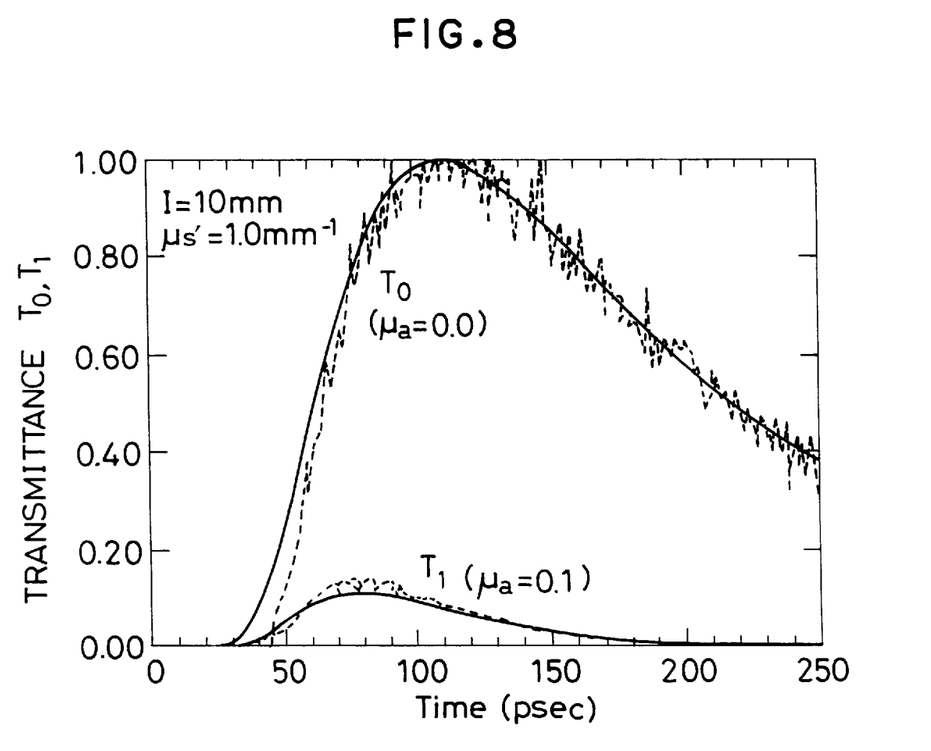
FIG. 8 is a graph of changes in the intensity of ultrashort pulses of transmitted light irradiated at an infinite slab, calculated based on the finite-element method and on the Monte Carlo method.

FIG. 8 is a graph of changes in the intensity of ultrashort pulses of transmitted light irradiated at an infinite slab 10 mm thick, calculated by the finite-element method and by the Monte Carlo method.

In the graph of FIG. 8, a solid line indicates values calculated by the finite-element method and a dotted line indicates values calculated by the Monte Carlo method. The results obtained by the two methods are in close agreement, showing that numerical analysis is also an effective way of calculating the reduced scattering and absorption coefficients of a light scattering material.

From the foregoing, it has been seen that with respect to light propagation, the method according to the present invention can be used to determine optical properties of light scattering material, including samples too small to be assumed to be an infinite or semi-infinite slab, randomly shaped samples, and samples having a distribution of optical properties.

The invention will now be described with reference to the following examples.

EXAMPLE 1

The relationship between BMD (bone mineral density g/cm$^3$) values of n samples of spinal bones (n is the number of samples) and optical properties was determined by a method described with reference to the second embodiment. The results are shown in Table 1. An increase in the BMD is accompanied by an increase in the reduced scattering coefficient $\mu s'$, showing what can be considered from a physical point of view.

TABLE 1

| BMD (g/cm$^2$) | $\mu s'$ (mm$^{-1}$) | $\mu a$ (mm$^{-1}$) |
|---|---|---|
| 0.091 | 1.42 | 0.075 |
| 0.123 | 1.75 | 0.096 |

EXAMPLE 2

The relationship between BMD (bone mineral density g/cm$^3$) values of samples of bovine thigh bone and optical properties was determined by a method described with reference to the first embodiment. The results are shown in Table 2.

TABLE 2

| | | BMD (g/cm$^2$) | $\mu s'$ (mm$^{-1}$) | $\mu a$ (mm$^{-1}$) |
|---|---|---|---|---|
| Trabecular | mean ± SD | 0.42 ± 0.15 | 1.59 ± 0.25 | 0.035 ± 0.013 |
| bone | min. | 0.22 | 1.08 | 0.015 |
| (n = 39) | max. | 0.62 | 2.13 | 0.090 |
| Cortical | mean ± SD | 1.50 ± 0.03 | 5.31 ± 0.26 | 0.014 ± 0.005 |
| bone | min. | 1.47 | 5.06 | 0.011 |
| (n = 6) | max. | 1.52 | 5.57 | 0.019 |

EXAMPLE 3

Figure 9:
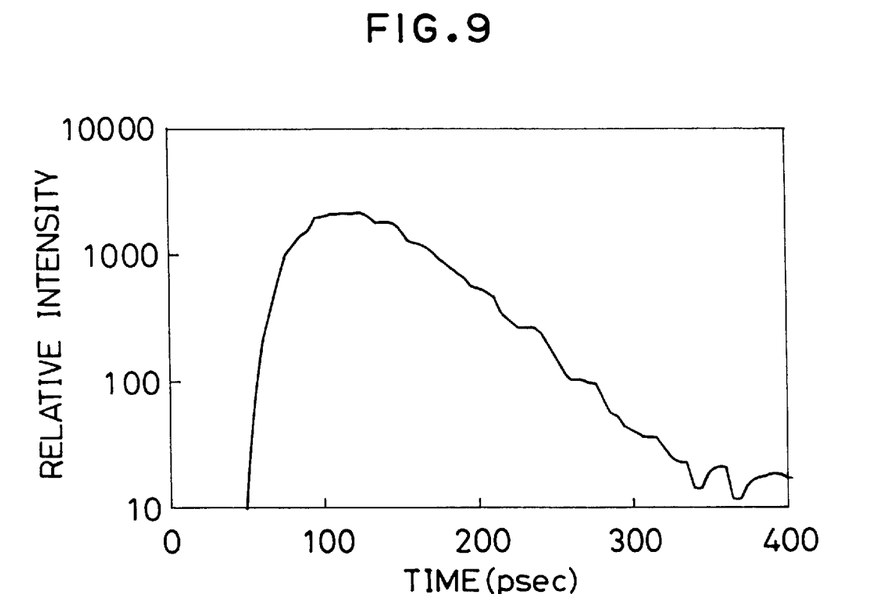
FIG. 9 is a graph of temporal changes in the intensity of transmitted light occurring when a bone sample was irradiated with picosecond pulses of light.
Figure 10:
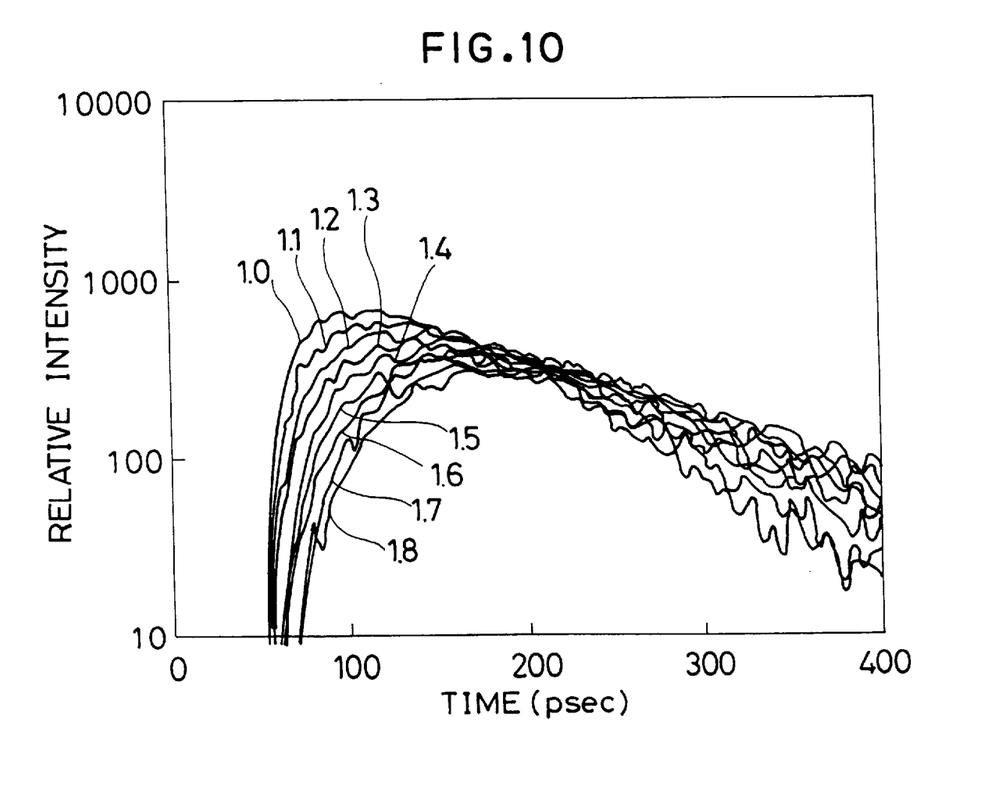
FIG. 10 is a graph showing simulated waveforms of transmitted light intensity over a picosecond coefficient $\mu s'$ resolution range of 1.0 to 1.8, based on a Monte Carlo simulation.

Bone samples cut into 10 mm cubes were irradiated with picosecond pulses of light and temporal changes in transmitted light intensity were measured. FIG. 9 is the result of the measurements. The temporal changes in transmitted light intensity obtained were stored in memory. Temporal changes in transmitted light intensity were then calculated, using a Monte Carlo simulation in which samples were assumed to be 10 mm cubes. For bone samples, an absorption coefficient $\mu a$ of 0 was used, and with the reduced scattering coefficient $\mu s'$ estimated to be in the range 1.2 to 1.6, as shown in FIG. 10, 0.1 increments were used. In FIG. 10, 1.0 indicates a $\mu s'$ of 1.0 mm$^{-1}$, 1.1 indicates a $\mu s'$ of 1.1 mm$^{-1}$, and so on up to 1.8, which indicates a $\mu s'$ of 1.8 mm$^{-1}$.

Figure 11:
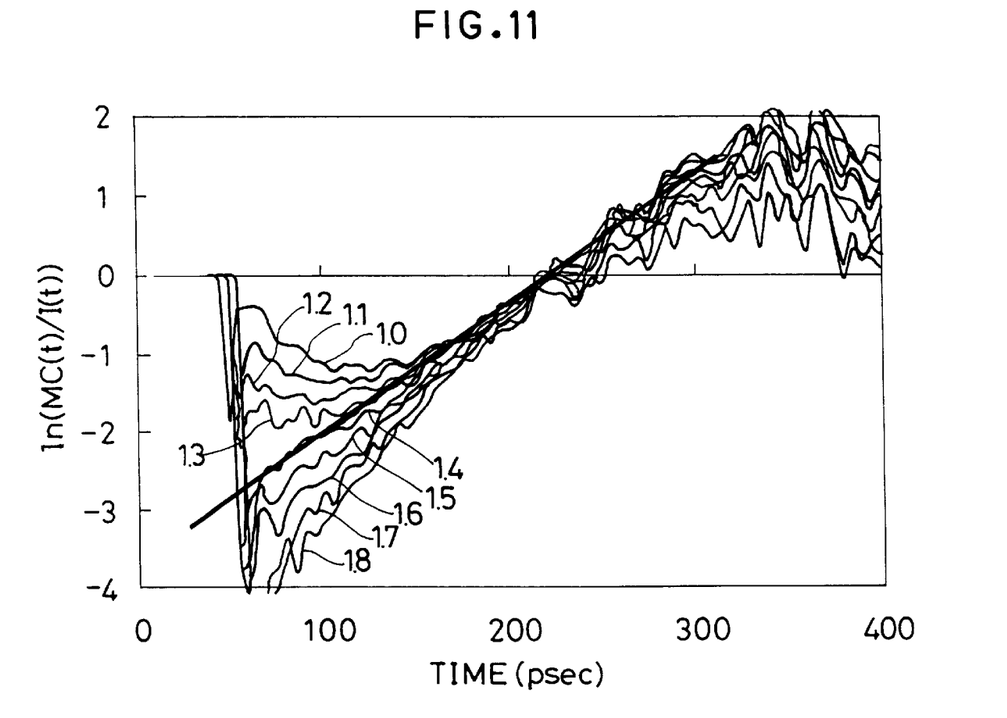
FIG. 11 is a graph showing temporal changes in log ln(MC(t)/I(t)) of the ratio of waveform (I(t)) to waveform (MC(t))

The time resolved transmittance (I(t)) of a bone sample shown in FIG. 9, a series of time resolved transmittances (MC(t)) obtained by simulation and a look-up table of optical properties were used to calculate ln(MC(t)/I(t)), the log of the ratio of time resolved transmittance (I(t)) to transmittances (MC(t)). The results are shown by FIG. 11, from which it can be seen that when a coefficient $\mu s'$ of the sample was in agreement with a coefficient $\mu s'$ used to simulate a standard transmittance, the log of the above ratio ln(MC(t)/I(t)) was linear, so the linearity of the curve of the log ratio for each coefficient $\mu s'$ was evaluated. As mentioned, in the graph 1.0 indicates a $\mu s'$ of 1.0 mm$^{-1}$, 1.1 a $\mu s'$ of 1.1 mm$^{-1}$, and so on up to 1.8 indicating a $\mu s'$ of 1.8 mm$^{-1}$.

From FIG. 11, it can be seen that the second half of ln(MC(t)/I(t)) is more or less linear regardless of the coefficient $\mu s'$ used in the simulation. So, a first-order regression line was calculated with respect to ln(MC(t)/I(t)) from 150 to 300 picoseconds, a first-order regression line was calculated with respect to ln(MC(t)/I(t)), and the sum of deviations from this first-order regression line in the first half of ln(MC(t)/I(t)) (60 to 150 picoseconds) was calculated.

Figure 12:
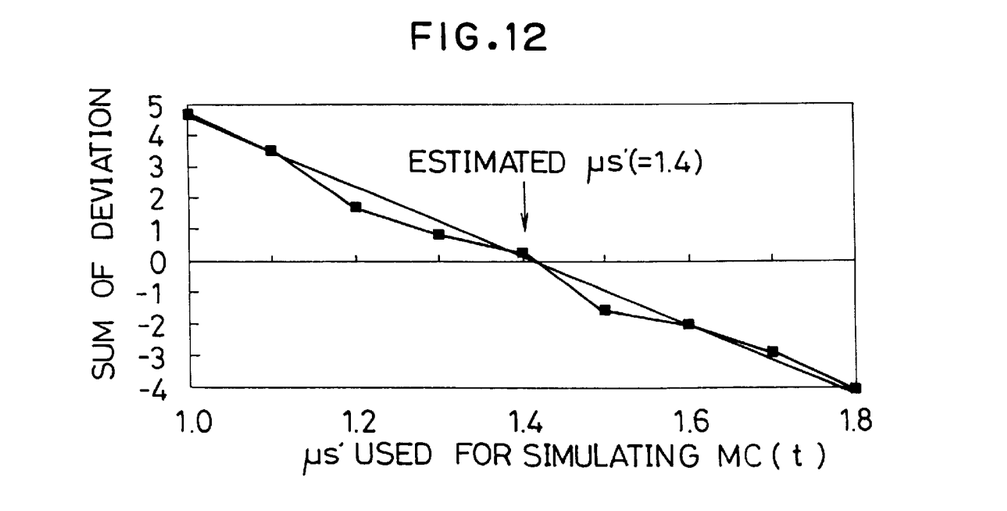
FIG. 12 is a graph based on the results of obtaining a first-order regression line of the second half of each log ln(MC(t)/I(t)) and the sum of deviations of the first half.

Thus, with respect to ln(MC(t)/I(t)) of each coefficient $\mu s'$, the sum of deviations in the first half (60 to 150 picoseconds) from the first-order regression line of the second half (150 to 300 picoseconds) was calculated and plotted against the $\mu s'$ coefficients used to produce time resolved transmittance MC(t), resulting in the graph of FIG. 12. In FIG. 12, the ordinate shows the sum of the deviation from the regression line of the second half of ln(MC(t)/I(t)), and the abscissa shows the coefficient $\mu s'$ used to produce time resolved transmittance MC(t). When noise prevents perfect linearity, a first-order regression line can be obtained with respect to this plot, as shown in FIG. 12. The value at the crossover point (i.e., a deviation of zero) is the $\mu s'$ of the sample. In this example, the $\mu s'$ of a bone sample was estimated to be 1.4 mm$^{-1}$, as indicated by the arrow.

Figure 13:
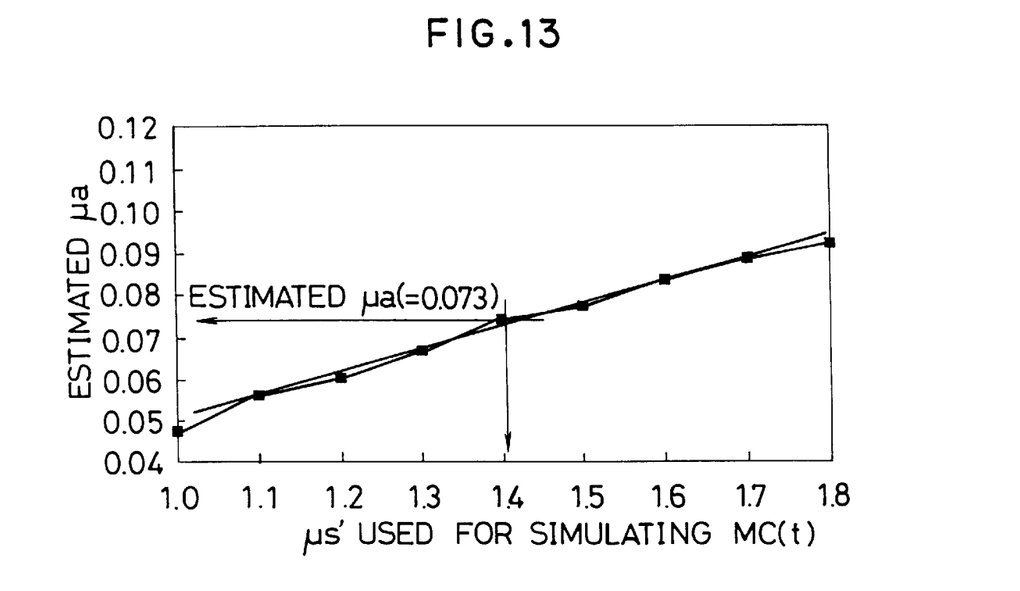
FIG. 13 is a graph obtained by calculating the slope of the first-order regression line of the second half of each log ln(MC(t)/I(t)) and plotting waveform MC(t) as a function of the reduced scattering coefficient $\mu s'$.

The slope of the first-order regression line for the second half (150 to 300 picoseconds) of ln(MC(t)/I(t)) of each coefficient $\mu s'$ was calculated and plotted against the coefficient μs' used to produce time resolved transmittance MC(t). The plot is shown in FIG. 13, in which the ordinate is the estimated absorption coefficient μa and the abscissa shows the reduced scattering coefficients μs' used to produce time resolved transmittance MC(t). As described above, when noise prevents perfect linearity, a first-order regression line is obtained. As described above, an estimate of 1.4 mm$^{-1}$ was used as the scattering coefficient μs' of the sample, so the value of the y coordinate at the intersection point with X=1.4 is the sample's absorption coefficient μa, so the estimated absorption coefficient μa in the case of this sample was 0.073 mm$^{-1}$.

Figure 14:
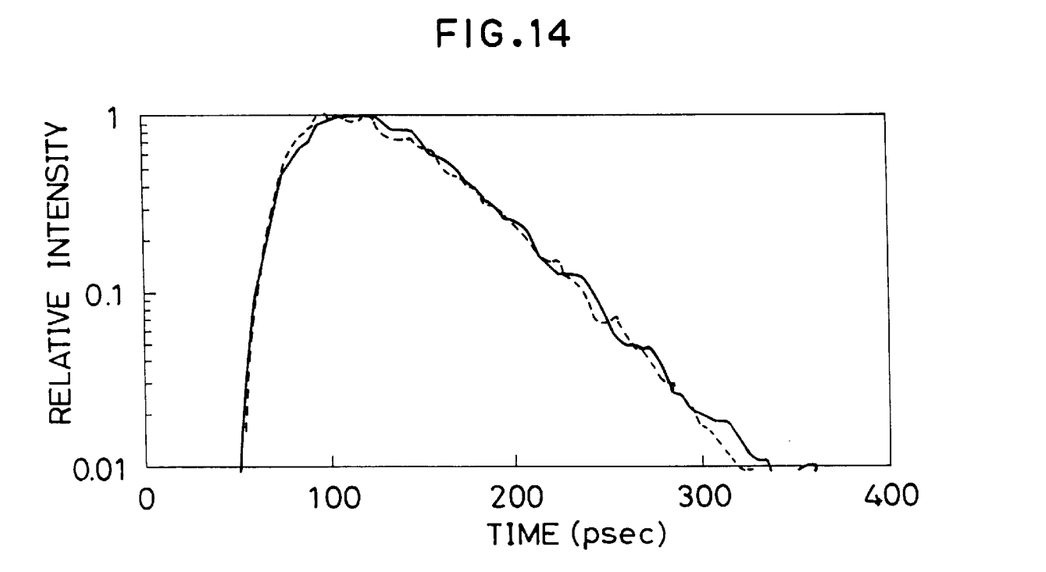
FIG. 14 is a graph showing a time resolved waveform of a bone sample and a time resolved waveform obtained by Monte Carlo simulation, in accordance with the present invention.

To verify that the coefficients μs' and μa obtained by the above procedure were the right values, a comparison was made between a picosecond time-resolved transmittance of the light pulses through the bone sample, and the transmittance obtained by Monte Carlo simulation using a scattering coefficient μs' of 1.4 mm$^{-1}$ and an absorption coefficient μa of 0.073 mm$^{-1}$ determined in accordance with the method of the invention. The transmittances are shown in FIG. 14, in which the solid line is the time-resolved transmittance of the bone sample, and the broken line is the simulated transmittance. This confirmed that there was close agreement between the two transmittances, and that the values of optical properties estimated from the invention were appropriate.

What is claimed is:

1. A method for determination of optical properties of light scattering material, comprising:

a step of numerically calculating and storing beforehand time response characteristics at a prescribed point on a scattering material sample in respect of numerous combinations of reduced scattering coefficients and absorption coefficients;

a step of irradiating light pulses at the sample and measuring time response characteristics of output light at a prescribed point;

a step in which agreement or similarity between a measured time response characteristic and any stored time response characteristic is analyzed by comparing the characteristics including calculating a log of a ratio of measured time response characteristics of output light to calculated time response characteristics for each time, and selecting a calculated time response characteristic at which the calculation outcome is linear or can be regarded as linear relative to time; and a step in which a reduced scattering coefficient and absorption coefficient of the sample are determined from an outcome of the analysis.

2. The method according to claim 1, wherein the numerical calculation is by a Monte Carlo method.

3. The method according to claim 1, wherein the numerical calculation is by a numerical analysis method.

4. The method according to claim 1, wherein wavelength of the light pulses is from a wavelength of visible light to 2 μm.

5. A method for determination of optical properties of light scattering material, comprising:

a step of numerically calculating and storing beforehand time response characteristics at a prescribed point on a scattering material sample in respect of numerous equivalent scattering coefficients and an absorption coefficient of zero;

a step of irradiating light pulses at the sample and measuring time response characteristics of output light at a prescribed point;

a step of calculating a log of a ratio of measured time response characteristics to stored time response characteristics for each time, and selecting a time response characteristic at which the calculation outcome is linear or can be regarded as linear relative to time; and a step in which a stored equivalent scattering coefficient that provides the time response characteristic at which the calculation outcome is linear or can be regarded as linear is determined as a reduced scattering coefficient of the sample, and an absorption coefficient of the sample is determined from a slope of temporal change in the calculation outcome that is linear or can be regarded as linear.

6. The method according to claim 5, wherein the numerical calculation is by a Monte Carlo method.

7. The method according to claim 5, wherein the numerical calculation is by a numerical analysis method.

8. The method according to claim 5, wherein wavelength of the light pulses is from a wavelength of visible light to 2 μm.

9. An apparatus for determining optical properties of light scattering material, comprising:

means for numerically calculating and storing beforehand time response characteristics at a prescribed point on a scattering material sample in respect of numerous combinations of reduced scattering coefficients and absorption coefficients;

means of irradiating light pulses at the sample and measuring time response characteristics of output light at a prescribed point;

means of analyzing agreement or similarity between a measured time response characteristic and any stored time response characteristic by comparing the characteristics including means of calculating a log of a ratio of measured time response characteristics to stored time response characteristics for each time and selecting a time response characteristic at which the calculation outcome is linear or can be regarded as linear relative to time; and means of determining a reduce scattering coefficient and absorption coefficient of the sample from an outcome of the analysis.

10. The method according to claim 9, wherein the numerical calculation is by a Monte Carlo method.

11. The method according to claim 9, wherein the numerical calculation is by a numerical analysis method.

12. An apparatus for determining optical properties of light scattering material, comprising:

means for numerically calculating and storing beforehand time response characteristics at a prescribed point on a scattering material sample in respect of numerous reduced scattering coefficients and an absorption coefficient of zero;

means of irradiating light pulses at the sample and measuring time response characteristics of output light at a prescribed point;

means of calculating a log of a ratio of measured time response characteristics of output light to calculated time response characteristics for each time and selecting a stored time response characteristic at which the calculation outcome is linear or can be regarded as linear relative to time;

means that determines a stored reduced scattering coefficient that provides the time response characteristic at which the calculation outcome is linear or can be regarded as linear, as a reduced scattering coefficient of the sample, and determines an absorption coefficient of the sample from a slope of temporal change in the calculation outcome that is linear or can be regarded as linear.

13. The method according to claim 12, wherein the numerical calculation is by a Monte Carlo method.

14. The method according to claim 12, wherein the numerical calculation is by a numerical analysis method.

* * * * *